(12) United States Patent
Lee et al.

(10) Patent No.: US 8,748,398 B2
(45) Date of Patent: Jun. 10, 2014

(54) STROKE-TARGETING PEPTIDE AND USE THEREOF

(75) Inventors: Byung-Heon Lee, Daegu (KR); In S. Kim, Daegu (KR); Hyung Soo Han, Daegu (KR); Jeong Soo Yoo, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 590 days.

(21) Appl. No.: 12/995,934

(22) PCT Filed: Jun. 2, 2009

(86) PCT No.: PCT/KR2009/002937
§ 371 (c)(1),
(2), (4) Date: Feb. 1, 2011

(87) PCT Pub. No.: WO2009/148252
PCT Pub. Date: Dec. 10, 2009

(65) Prior Publication Data
US 2011/0150764 A1 Jun. 23, 2011

(30) Foreign Application Priority Data
Jun. 2, 2008 (KR) ........................ 10-2008-0051555

(51) Int. Cl.
*A61K 38/08* (2006.01)
*C07K 7/06* (2006.01)
*C12N 15/00* (2006.01)

(52) U.S. Cl.
USPC ................. 514/21.6; 530/328; 435/320.1

(58) Field of Classification Search
USPC ................. 514/21.6; 530/328; 435/320.1
See application file for complete search history.

(56) References Cited

U.S. PATENT DOCUMENTS 7,968,081 B2 * 6/2011 Lee et al. .................... 424/1.69

OTHER PUBLICATIONS

Hong et al. Jul. 19, 2008, Detection of apoptosis in a rat model of focal cerebral ischemia using a homing peptide selected from in vivo phage display, Journal of Controlled Release, 131: 167-172.*
Hong et al., Oct. 30, 2008, Phage display selection of peptides that home to atherosclerotic plaques: IL-4 receptor as a candidate target in atherosclerosis, J. Cell. Mol. Med., 12(5B): 2003-2014.*
International Search Report for PCT/KR2009/002937, mailed Feb. 16, 2010.

* cited by examiner

*Primary Examiner* — Amber D Steele
(74) *Attorney, Agent, or Firm* — Edwards Wildman Palmer LLP (57) ABSTRACT

The present invention relates to stroke-targeting peptides and use thereof. More specifically, the present invention relates to a stroke-targeting peptide comprising an amino acid sequence selected from the group consisting of SEQ ID NO: 1 to SEQ ID NO: 4 and use thereof. The peptide of the present invention can be specifically bound to stroke cells in the subject, and thus can be effectively used in diagnostic markers and kits for stroke, and compositions for drug delivery specific to stroke and pharmaceutical compositions and compositions for imaging stroke.

11 Claims, 4 Drawing Sheets

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: Stroke-targeting peptide 1

<400> SEQUENCE: 1

Cys Leu Glu Val Ser Arg Lys Asn Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Stroke-targeting peptide 2

<400> SEQUENCE: 2

Cys Lys Arg Gly Gly Ala Thr Ala Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Stroke-targeting peptide 3

<400> SEQUENCE: 3

Cys Arg Ser Ala Val Ala Lys Asn Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Stroke-targeting peptide 4

<400> SEQUENCE: 4
```

```
Cys Thr Lys Arg Asn Ala Pro Asp Cys
1               5

<210> SEQ ID NO 5
<211> LENGTH: 6
<212> TYPE: PRT
<213> ORGANISM: Rattus norvegicus

<400> SEQUENCE: 5

Glu Thr Ser Arg Lys Asn
1               5

<210> SEQ ID NO 6
<211> LENGTH: 6
<212> TYPE: PRT
<213> ORGANISM: Rattus norvegicus

<400> SEQUENCE: 6

Glu Pro Ser Arg Lys Asn
1               5

<210> SEQ ID NO 7
<211> LENGTH: 5
<212> TYPE: PRT
<213> ORGANISM: Rattus norvegicus

<400> SEQUENCE: 7

Glu Val Ser Arg Lys
1               5

<210> SEQ ID NO 8
<211> LENGTH: 7
<212> TYPE: PRT
<213> ORGANISM: Rattus norvegicus

<400> SEQUENCE: 8

Lys Arg Gly Gly Pro Thr Ala
1               5

<210> SEQ ID NO 9
<211> LENGTH: 7
<212> TYPE: PRT
<213> ORGANISM: Rattus norvegicus

<400> SEQUENCE: 9

Arg Ser Ala Val Thr Arg Asn
1               5

<210> SEQ ID NO 10
<211> LENGTH: 5
<212> TYPE: PRT
<213> ORGANISM: Rattus norvegicus

<400> SEQUENCE: 10

Lys Arg Asn Ala Pro
1               5
```

STROKE-TARGETING PEPTIDE AND USE THEREOF

CROSS-REFERENCE TO RELATED APPLICATION

The present application is a U.S. national entry of International Application No. PCT/KR2009/002937 (International Publication No. WO2009/148252) having an International filing date of Jun. 2, 2009, and claiming priority to Korean Application 10-2008-0051555 filed Jun. 2, 2008, both of which applications are incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 18, 2013, is named 87660-307161_ST25.txt and is 2,041 bytes in size.

TECHNICAL FIELD

The present invention relates to stroke-targeting peptides and use thereof. More particularly, it relates to stroke-targeting peptides comprising an amino acid sequence represented by anyone selected from the group consisting of SEQ ID NO: 1 to SEQ ID NO: 4 and use thereof.

BACKGROUND ART

A stroke is largely divided into two types of strokes. One is an ischemic stroke caused by an ischemic state of a brain tissue because of reduction or blocking of blood supply to the brain tissue, and the other is a hemorrhagic stroke causing bleeding in a brain tissue by rupture of a blood vessel. Since about 80% of all stroke patients have the ischemic stroke, and about one third of ischemic stroke patients undergo death, the ischemic stroke can be said to be a serious disease. Especially, the ischemic stroke is caused from insufficient cerebral circulation of blood, which is caused by the blocking of inflow of arterial blood. In general, appropriate supply of brain blood is secured by an arterial system within a brain. However, various diseases, including an inflammation, and atherosclerosis, may cause a thrombus, that is, a blood clot generated in a blood vessel. The thrombus may obstruct an arterial blood flow, thereby causing cerebral ischemia and its accompanying neurological conditions. In addition, the ischemic stroke may be caused when an embolus, that is, a piece of thrombus formed from a heart, blocks a blood vessel. It causes a decreased pressure of perfusion or an increased viscosity of blood as well as an inappropriate flow of brain blood.

There are two treatment methods capable of being used for the stroke. One method is to reduce a lack of oxygen and glucose in an artery by increasing a blood flow, and the other method is to protect a neuron by blocking nerve destruction induced by cerebral ischemia and excitotoxicity. Clinically used neuron protective agents include a calcium channel blocker, an MNDA receptor antagonist (a kind of glutamate receptor), and the like. However the treatment methods show a low effect while having a high incidence of side effects. Accordingly, it is urgently required to develop a method for increasing the effect of the treatment agent and significantly reducing side effects on a normal tissue.

Meanwhile, the method for diagnosing the stroke as described above is divided into a preventive diagnosis method, and an onset diagnosis method. The preventive diagnosis method representatively includes a blood test, and the onset diagnosis method includes a blood test, a transcranial Doppler method, a computed tomography method, a brain magnetic resonance imaging method, a cerebral angiography method, and the like. For the conventional preventive diagnosis method of a stroke, there is no authorized reliable blood test so far. For the onset diagnosis method, although various methods have been developed and clinically used, most of them can only determine an injured region, but there exists no diagnosis method for determining if the injured region is a penumbra capable of being recovered again and for predicting the prognosis of stroke treatment. Thus, there is a limitation in determining a treatment course.

Meanwhile, a drug delivery system or a target therapy which is for selectively delivering a drug to a specific tissue has been a highly interesting technology. This is because even though a therapeutic agent is used in the same amount, it is possible to increase the effect of the drug, and at the same time to highly reduce the side effects on a normal tissue. In addition, when the system or therapy is applied to a gene therapy, it is possible to increase the therapy efficiency and to reduce serious side effects by selectively delivering a virus to a specific tissue. For this, an antigen specific to a specific tissue, and an antibody targeting such an antigen have been mainly developed so far. However, in a case of an antibody, there is a problem such as an anxiety about an immune response, a low efficiency in tissue penetration, and the like. On the other hand, a peptide is advantageous in that due to its low molecular weight, an anxiety about an immune response is low, and its penetration into a tissue is easy. Accordingly, when a target peptide is connected with a conventional therapeutic agent, it can be utilized as an intellectual drug delivery carrier for selectively delivering a drug to a specific tissue. Thus, it is required to develop a target peptide.

DISCLOSURE

Technical Problem

Accordingly, the inventors of the present invention have worked to develop stroke-targeting peptides for treatment and diagnosis of stroke. While researching, we searched stroke tissue-specific peptides using phage peptide display technique and verified that the peptides could be useful as diagnostic markers for stroke and intelligent drug carrier, and completed the present invention.

Accordingly, an object of the present invention is to provide a stroke-targeting peptide comprising an amino acid sequence selected from the group consisting of SEQ ID NO: 1 to SEQ ID NO: 4.

In another aspect, an object of the present invention is to provide a polynucleotide comprising a nucleotide sequence encoding the peptide.

In another aspect, an object of the present invention is to provide a diagnostic marker for stroke comprising the peptide.

In another aspect, an object of the present invention is to provide a diagnosis kit for stroke comprising the peptide.

In another aspect, an object of the present invention is to provide a composition for drug delivery specific to stroke comprising the peptide.

In another aspect, an object of the present invention is to provide a pharmaceutical composition for preventing or treating stroke comprising the peptide as an effective ingredient.

In another aspect, an object of the present invention is to provide a composition for imaging stroke comprising the peptide.

In another aspect an object of the present invention is to provide an use of the peptide for diagnosis of stroke.

In another aspect, an object of the present invention is to provide a method for diagnosis of stroke administering to a subject in need thereof an effective amount of the peptide and a label bound thereto; and determining binding the peptide to a stroke cell and a site of the binding.

In another aspect, an object of the present invention is to provide an use of the peptide for drug delivery.

In another aspect, an object of the present invention is to provide a method for drug delivery comprising administering to a subject in need thereof an effective amount of the peptide of claim 1 and an agent bound thereto.

In another aspect, an object of the present invention is to provide an use of the peptide and an anti-stroke agent bound thereto for preparing agents for treating stroke.

In another aspect, an object of the present invention is to provide a method for treating stroke comprising administering to a subject in need thereof an effective amount of the peptide and an anti-stroke agent bound thereto.

In another aspect, an object of the present invention is to provide an use of the peptide of claim 1 for imaging stroke lesion.

In another aspect, an object of the present invention is to provide a method for imaging stroke lesion comprising administering to a subject in need thereof an effective amount of the peptide and a label bound thereto.

Technical Solution

To attain the object, the present invention provides a stroke-targeting peptide comprising an amino acid sequence selected from the group consisting of SEQ ID NO: 1 to SEQ ID NO: 4.

In another aspect, the present invention provides a polynucleotide comprising a nucleotide sequence encoding the peptide.

In another aspect, the present invention provides a diagnosis kit for stroke comprising the peptide.

In another aspect, the present invention provides a diagnosis kit for stroke comprising the peptide In another aspect, the present invention provides composition for drug delivery specific to stroke comprising the peptide.

In another aspect, the present invention provides a pharmaceutical composition for preventing or treating stroke comprising the peptide as an effective ingredient.

In another aspect, the present invention provides a composition for imaging stroke comprising the peptide.

In another aspect, the present invention provides a use of the peptide for diagnosis of stroke.

In another aspect, the present invention provides a method for diagnosis of stroke administering to a subject in need thereof an effective amount of the peptide and a label bound thereto; and determining binding the peptide to a stroke cell and a site of the binding.

In another aspect, the present invention provides an use of the peptide for drug delivery.

In another aspect, the present invention provides a method for drug delivery comprising administering to a subject in need thereof an effective amount of the peptide of claim 1 and an agent bound thereto.

In another aspect, the present invention provides an use of the peptide and an anti-stroke agent bound thereto for preparing agents for treating stroke.

In another aspect, the present invention provides a method for treating stroke comprising administering to a subject in need thereof an effective amount of the peptide and an anti-stroke agent bound thereto.

In another aspect, the present invention provides an use of the peptide of claim 1 for imaging stroke lesion.

In another aspect, the present invention provides a method for imaging stroke lesion comprising administering to a subject in need thereof an effective amount of the peptide and a label bound thereto.

Hereafter, the present invention will be described in detail.

In the present invention, a term of "stroke" indicates a syndrome caused by a blood circulation disorder of a brain, which is accompanied by urgent consciousness disturbance and motor paralysis. The region where the stroke occurs is largely divided into an umbra, that is, an irreversible injured region, and a penumbra having a possibility of recovery which wraps the umbra. As long as it is not specially noted in the present invention, the stroke includes injury in both an umbra and a penumbra.

As used herein, the "diagnosis" refers all kinds of analysis determining prediction of disease genesis, risk rate of disease genesis and prognosis after treatment.

As used herein, the "effective amount" refers to the amount effective in treating the subject diseases.

As used herein, the "subject" refers to mammals, particularly, animals comprising human. The subject may be human in need of treatment.

The peptide of the present invention has an amino acid sequence selected from the group consisting of SEQ ID NO: 1 to SEQ ID NO: 4. More preferably, the above peptide of the present invention may be an amino acid sequence represented by SEQ ID NO: 1. The peptide of the present invention is characterized by specifically binding to stroke tissue.

A peptide of the present invention comprises all kinds of peptide, protein, mimetic peptide, compound and biological agent, which is capable of specifically binding to apoptotic cells. The peptide of the present invention may be derived from the nature or may be synthesized by a known peptide synthesis technique.

In addition, the peptide of the present invention may comprise the peptide having naturally occurring amino acid sequences and variants having modified sequences as well. The variants of the peptide of the present invention refer to peptides having different sequences from the amino acid sequence selected from the group consisting of SEQ ID NO:1 to SEQ ID NO:4, prepared by deletion, insertion, non-conserved or conserved substitution, substitution of amino acid analog or their combinations. The silent alteration of amino acid residues not to substantially impair protein activity is well known to one skilled in the art (H. Neurath, R. L. Hill, The Proteins, Academic Press, New York, 1979).

In addition, the peptide of the present invention may comprise modifications such as phosphorylation, sulfation, acrylation, glycosylation, methylation, farnesylation and the like.

In one embodiment of the present invention, an animal model whose brain's one side hemisphere was locally stroke-induced, was obtained (see <Example method 1>), and then a phage-displayed peptide library method (see <Example method 2>) was carried out. As a result, it was found that a peptide comprising an amino acid sequence selected from the group comprising SEQ ID Nos. 1 to 4 was bound to or targeted to a stroke tissue (see <Example result 1>, and Table 1).

In addition, in another embodiment of the present invention, from among the peptides, a peptide comprising an amino acid sequence (CLEVSRKNC) (SEQ ID No. 1), with the highest frequency of occurrence at a stroke tissue, was selected. Then, when a phage comprising the peptide displayed thereon was injected to a stroke-induced animal model, it was determined that the phage was specifically bound to a stroke tissue (see <Example result 2>, and FIG. 1).

Figure 2:
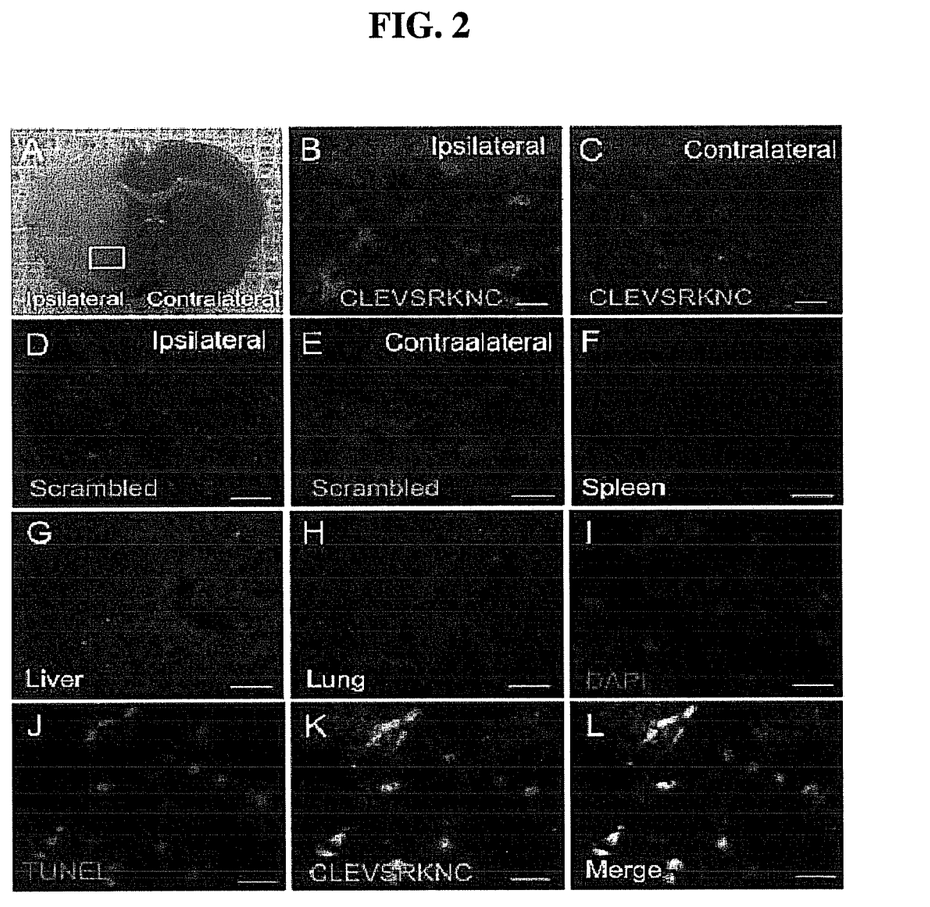
FIG. 2 is the photograph showing CLEVSRKNC peptide (SEQ ID NO: 1) is targeted to stroke tissue in vivo and could detect cell apoptosis from stroke tissue.

In addition, in a further embodiment of the present invention, in order to determine if the specific targeting of the phage was caused by the peptide displayed on the phage, the peptide was synthesized and injected. As a result, it was found that the peptide of the present invention was specifically bound to a stroke tissue, and especially bound to a stroke cell of a penumbra. In addition, it was found that it was not bound to a control group organ such as a spleen, a liver, and a lung. In addition, when an apoptosis analysis was carried out by using TUNEL staining, it was found that the peptide can detect the apoptosis in a stroke tissue, and especially, it was specifically bound to a penumbra in a stroke region (see <Example result 3>, and FIG. 2).

Figure 3:
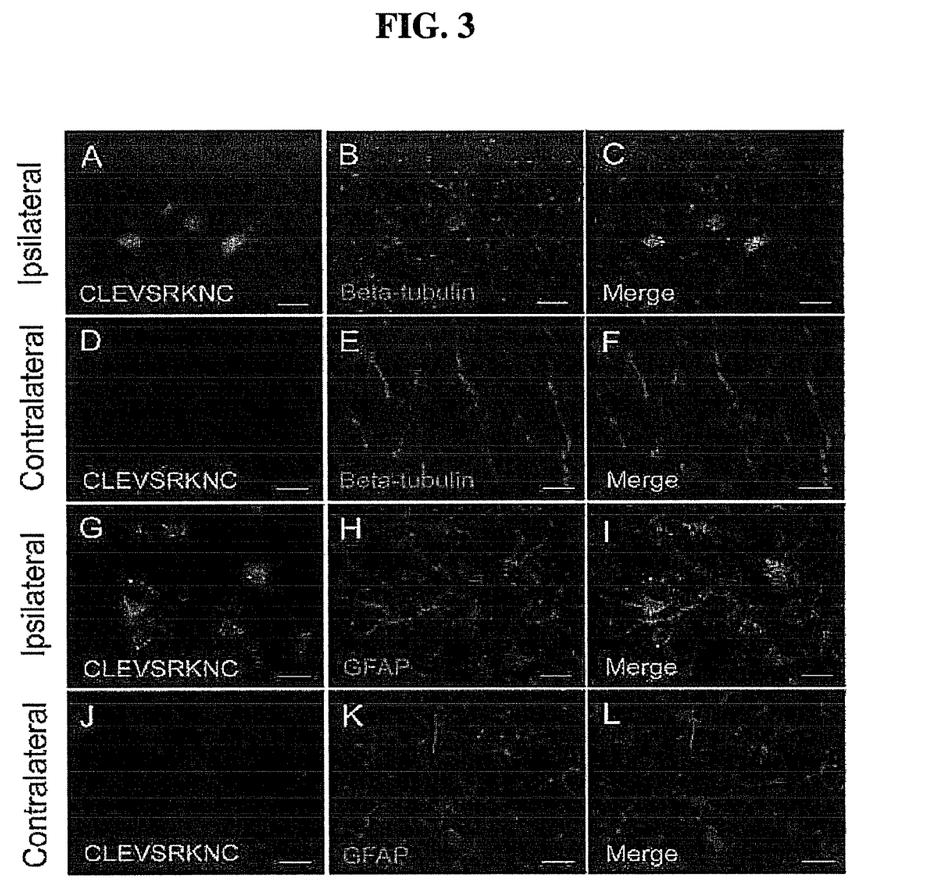
FIG. 3 is the photograph analyzing the type of cell components which bind to inducing CLEVSRKNC peptide (SEQ ID NO: 1) in vivo by immune fluorescence staining.

In addition, in a still further embodiment of the present invention, in order to analyze the type of a cell bound to the peptide of the present invention in a stroke tissue, an immunofluorescence staining method was carried out by using an antibody specific to a cell type. As a result, the peptide of the present invention was determined to be specifically disposed at the same position as β-tubulin-positive neuron cell in the stroke tissue (see <Example result 4>, and FIG. 3).

Figure 4:
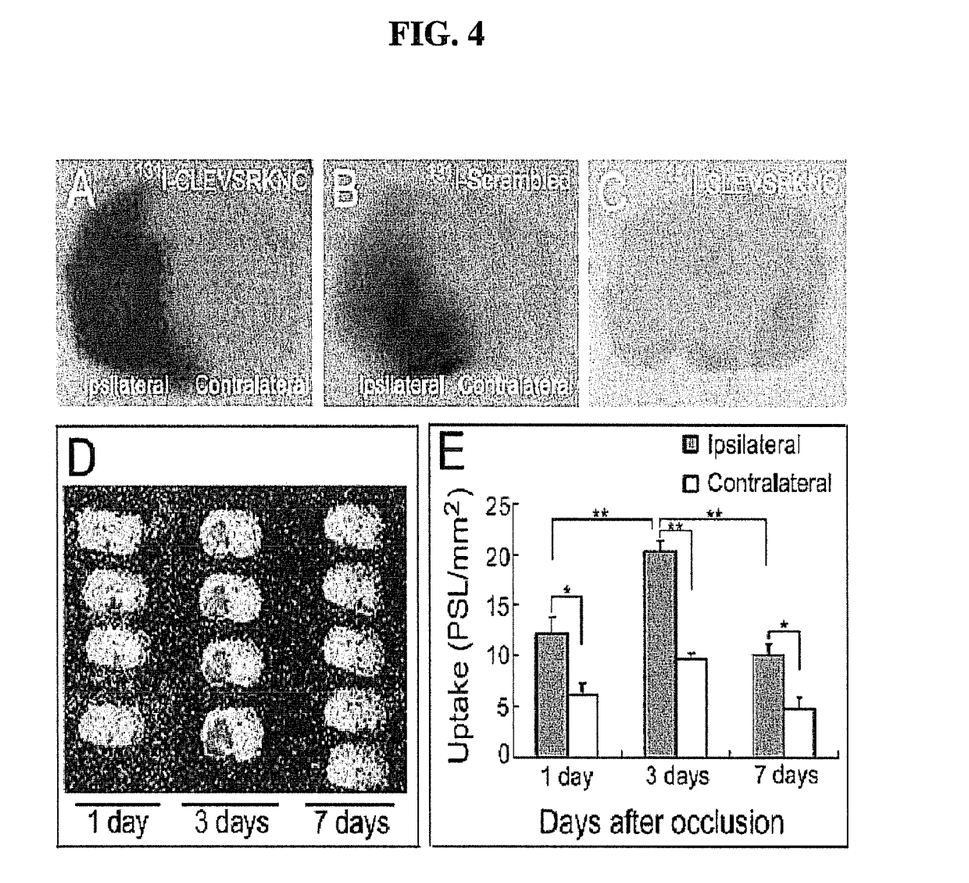
FIG. 4 is the photograph showing the result of autoradiography regarding absorption of CLEVSRKNC peptide (SEQ ID NO: 1) which is label radioactive isotope in ischemic stroke tissue.

In addition, in a still further embodiment of the present invention, the peptide of the present invention was labeled with a radioisotope, and subjected to autoradiography. As a result, it was determined that the peptide of the present invention was specifically observed in a stroke tissue (see <Example result 5>, and FIG. 4). Especially, the finding that the radiation absorption was increased on the first day from the onset of a stroke, reached a peak on the third day, and reduced on the seventh day, corresponded to a conventional research result that apoptosis caused by a stroke was the highest on the first to third day from the onset (U. Dirnagl, C. Iadecola, M. A. Moskowitz; Pathobiology of ischemic stroke: an integrated view, Trends Neurosci. 22(9): 391-397, 1999).

Accordingly, the peptide of the present invention can be usefully used for diagnosis and treatment of a stroke by being specifically bound to a stroke tissue. Especially, since the peptide of the present invention is induced into a stroke tissue within 15 minutes from its in-vivo administration, it can be usefully used for quick diagnosis of a stroke (see <Example result 3>). The stroke is preferably an ischemic stroke, but the present invention is not limited thereto. In addition, the peptide of the present invention is specifically bound to a penumbra of a stroke region, and thus can be usefully used for detecting and quantifying the penumbra.

The peptide of the present invention may be easily prepared by chemical synthesis known in the art (Creighton, Proteins; Structures and Molecular Principles, W. H. Freeman and Co., NY, 1983). The representative method includes liquid-phase or solid-phase synthesis, fragment condensation, F-MOC or T-BOC chemistry, and the like, but the present invention is not limited thereto (Chemical Approaches to the Synthesis of Peptides and Proteins, Williams et al., Eds., CRC Press, Boca Raton Fla., 1997; A Practical Approach, Athert on & Sheppard, Eds., IRL Press, Oxford, England, 1989). In addition, the peptide of the present invention may be prepared by a genetically engineered method. First, according to a conventional method, a DNA sequence coding the peptide is constructed. The DNA sequence may be constructed through PCR amplification by using an appropriate primer. In another method, according to a standard method known in the art, for example, a DNA sequence may be synthesized by using an automatic DNA synthesizer (commercially available from Biosearch or Applied Biosystems). The constructed DNA sequence is inserted into a vector which is operatively linked to the DNA sequence and includes one or more expression control sequences (e.g., a promoter, an enhancer, etc.) for controlling the expression of the DNA sequence, and then the recombinant expression vector from this is used for transforming a host cell. The produced transformant is cultured in a medium and a condition, enough to express the DNA sequence, and then from the culture, a substantial pure peptide coded by the DNA sequence is recovered. The recovery may be carried out by using a method known in the art (e.g., chromatography). The 'substantial pure peptide' means that the peptide according to the present invention substantially does not include any other proteins derived from host cells. The genetically engineered method for synthesizing the peptide of the present invention can be found in the reference mentioned below: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y., Second (1998) and Third (2000) Edition; Gene Expression Technology, Method in Enzymology, Genetics and Molecular Biology, Method in Enzymology, Guthrie & Fink (eds.), Academic Press, San Diego, Calif., 1991; and Hitzeman et al., J. Biol. Chem., 255:12073-12080, 1990.

The polynucleotide of the present invention is characterized in that it has a base sequence for encoding the peptide of the present invention. Specifically, the polynucleotide is characterized in that it encodes a stroke-targeting peptide comprising an amino acid sequence selected from the group comprising SEQ ID Nos. 1 to 4. The polynucleotide of the present invention may be usefully used for producing the peptide of the present invention by general expression. In conclusion, the base sequence of the polynucleotide can have any combinations as long as they can encode the peptide of the present invention.

In addition, the present invention provides a vector comprising a base sequence encoding the peptide of the present invention, and a transformant transformed by the vector.

The vectors of the present invention include a plasmid vector, a cosmid vector, a bacteriophage vector and a viral vector, but are not limited thereto. The vectors of the present invention may conventional cloning vectors or expression vectors, and the expression vectors comprise regulatory elements for gene expression such as a promoter, operator, an initiation codon, a stop codon, a polyadenylation signal, and an enhancer (promoting gene), and a variety of vectors can be prepared according to the purpose. Furthermore, the said vectors may comprise selective labels for selecting host cells comprising the vector and in case of replicable vectors, they comprise replication origin.

The transformation with the said vector can be carried out according to any known transformation method in the pertinent art. Preferably, microprojectile bombardment, electroporation, $CaPO_4$ precipitation, $CaCl_2$ precipitation, PEG-mediated fusion, microinjection and liposome-mediated method, but not limited to. The transformant may be *Escherichia coli, Bacillus subtilis, Streptomyces, Pseudomonas, Proteus mirabilis* and *Staphylococcus, Agrobacterium tumefaciens*, but not limited to.

Accordingly, a label of the present invention is characterized by capable for diagnosis of stroke comprising the peptide of the present invention. The stroke is preferably, not limited thereto, ischemic stroke.

The diagnosis of a stroke using a peptide of the present invention may be easily carried out by preferably detecting a stroke cell of an individual under suspicion of a stroke. In addition, it is possible to diagnosing a stroke by reacting a brain tissue or a brain cell, directly obtained through a biopsy from an individual under the suspicion of the stroke, with the peptide of the present invention, and then detecting the binding thereof. For more accurate diagnosis, as a control group, a binding of a brain cell of a normal individual to the peptide of the present invention may be detected. The diagnosis of a stroke may be carried out by detecting a signal (e.g., fluorescence quenching) indicating a binding of a stroke cell to the peptide of the present invention. The above described method for finding a stroke cell, in which the stroke-targeting peptide of the present invention is marked with a detectable label, and is reacted with a brain cell, and then a signal indicating a binding of a stroke cell to the peptide of the present invention is detected, is more accurate than a staining method conventionally used for stroke diagnosis.

Furthermore, the peptide of the present invention may be used to diagnose a stroke in a living body. For example, the peptide of the present invention, marked with a fluorescent material, is injected into a brain, and then is reacted with a brain cell. Then, an image device capable of detecting a fluorescent material within a living body can be used to find a stroke cell.

In addition, the kit of the present invention is characterized in that it includes the peptide of the present invention and can diagnose a stroke. Furthermore, the present invention provides an use of the peptide of the present invention for diagnosis of stroke. In addition, the present invention provides a method of diagnosing a stroke, the method comprising the steps of: (a) administering to a subject in need thereof an effective amount of the peptide of claim 1 and a label bound thereto, wherein the label is selected from the group consisting of chromogenic enzymes, radioisotopes, chromophores, light emitting materials, fluorescers, super paramagnetic particles, and ultrasuper paramagnetic particles; and (b) determining binding the peptide to a stroke cell and a site of the binding in the subject.

The stroke is preferably, not limited thereto, ischemic stroke. The peptide of the present invention which comprises the diagnosis kit may be synthesized easily by method mentioned below. Otherwise, for easy identification, detection and qualification of binding the peptide of the present invention to stroke cell, the peptide of the present invention may be provided as a form of labeled. In other words, the peptide could be provided with linked (for example, covalent bond or crosslink) to a detectable label material. The said detectable label material may be coloring enzyme (for example, peroxidase, alkaline phosphatase), radioactive isotope (for example, $^{18}F$, $^{124}I$, $^{125}I$, $^{32}P$, $^{35}S$), chromophore, scintillating materials or fluorescent materials (for example: FITC, RITC, fluorescent proteins (GFP (Green Fluorescent Protein); EGFP (Enhanced Green Fluorescent Protein), RFP (Red Fluorescent Protein); DsRed (*Discosoma* sp. red fluorescent protein); CFP (Cyan Fluorescent Protein), CGFP (Cyan Green Fluorescent Protein), YFP (Yellow Fluorescent Protein), Cy3, Cy5 and Cy7.5), super paramagnetic particles or ultrasuper paramagnetic particles. Similarly, the said detectable label material may be an antibody, an epitope, a substrate, cofactor, inhibitor or compatible ligand. The labeling may be performed while peptide synthesis steps of the present invention or may be performed additional to already synthesized peptide. By which, diagnosis and molecular imaging of stroke could be performed easily.

Detection techniques based on labeling are well known in the art. Detections may be made, for example, as follows. In case a fluorescent material is used as a detectable label, immunofluorescence staining may be employed for diagnosis of stroke. For example, the peptide of the present invention labeled with a fluorescent material may be reacted with brain cells, and, fluorescence emitted by the peptide may be observed under a fluorescence microscope. When the fluorescence is observed, it would be diagnosed as stroke. In addition, in case that an enzyme is used as a detectable label, absorbance may be measured following an enzymatic reaction with a substrate, and, in case that a radioactive material is used, a radioactive radiation may be measured. Accordingly, stroke could be diagnosed by detecting stroke cells.

The kit of the present invention may further include, besides the peptide of the present invention, a buffer solution, a culture medium, a control group cell (normal brain cell), which are appropriate for a binding reaction between the peptide and a stroke cell. In addition, in a case where the peptide of the present invention is provided without label, a detectable label for peptide may be further included in the kit. Alternatively, an antibody against the peptide of the present invention, a secondary antibody marked with a fluorescent material, a chromogenic substrate, etc. may be further included in the kit. The antibody against the peptide of the present invention may be prepared according to a conventional antibody preparing method known in the art, as described above.

In addition, the peptide of the present invention may be provided by being coated on the surface of a plate. In this case, a brain cell is directly inoculated into the plate and is reacted in an appropriate condition, and then the stroke may be diagnosed by observing the binding of a stroke cell to the peptide, on the surface of the plate.

It is apparent to those skilled in the art that the test processes, the test agents, and the reaction conditions used in the methods may be conventionally known in the art.

In addition, the peptide of the present invention can be specifically bound to a stroke cell, and thus can be used as a smart drug delivery carrier for selectively delivering a drug to the cell. Accordingly, there is provided a drug delivery composition comprising the peptide of the present invention as an active component. In addition, there are provided drug delivery uses of the peptide of the present invention. Furthermore, there is provided a drug delivery method in which the peptide of the present invention and a drug bound thereto are administered to an individual requiring them in an effective dose.

In addition, the drug delivery composition, its use, and the drug delivery method, according to the present invention, are characterized in that they are specific to a stroke. The drug indicates a stroke therapeutic agent, and the stroke preferably indicates an ischemic stroke, but the present invention is not limited thereto.

The peptide of the present invention may be used as a smart drug delivery carrier for selectively delivering a drug such as a stroke therapeutic agent to a stroke tissue. In a case where the peptide of the present invention is used for stroke treatment in connection with a conventional stroke therapeutic agent, since the stroke therapeutic agent is selectively delivered to only by a stroke cell by the peptide of the present invention, it is possible to increase the efficacy of the drug, and at the same time to significantly reduce the side effects of the stroke therapeutic agent on a normal tissue.

There is no limitation in the stroke therapeutic agent which can be in connection with the peptide of the present invention as long as it is conventionally used in stroke treatment. The stroke therapeutic agent is preferably selected from the group comprising a calcium channel blocker, glutamate, an NMDA receptor antagonist, an antioxidant, an apoptosis inhibitor, and minocycline-based antibiotics. The connection of the therapeutic with the peptide of the present invention may be carried out by a method known in the art, for example, covalent bonding, crosslinking, etc. For this, the peptide of the present invention, as required, may be chemically modified in a range where its activity is not destroyed.

In addition, a pharmaceutical composition of the present invention is the pharmaceutical composition for prevention or treatment of stroke comprising the peptide of the present invention as an active ingredient. In addition, the present invention provides a use of the peptide of the present invention and an anti-stroke agent bound thereto for preparing reagent for treatment of stroke. In addition, the present invention provides a method for treatment of stroke comprising administering the peptide and an anti-stroke agent bound thereto to a subject in need thereof at an effective dose. A pharmaceutical composition, a use and a method for treatment of the present invention could be used for prevention or treatment of stroke by comprising the peptide of the present invention and delivering reagent such as a reagent for treatment of stroke selective to stroke cells. The reagent preferably refers to reagent for treatment of stroke and the stroke refers preferably, but not limited thereto, ischemic stroke.

Meanwhile, a pharmaceutical composition of the present invention may be formulated into pure form or appropriate forms with pharmaceutically acceptable carriers. As used herein, the term "pharmaceutically acceptable" means nontoxic composition which is physiologically acceptable and, when administered to human beings, generally does not cause allergic reactions, such as gastrointestinal disorder and dizziness, or similar reactions thereto. The said carriers may comprise all kinds of solvents, dispersing medium, water-in-oil or oil-in-water emulsion, aquatic composition, liposome, microbead and microsome, biodegradable nanoparticles.

Meanwhile, the pharmaceutical composition of the present invention may be formulated with appropriate carriers according to administration routes. These formulations are described in *Remington's Pharmaceutical Science*, 15th Edition, 1975, Mack Publishing Company, Easton, Pa. which is well know prescription manual.

Another carrier which is pharmaceutically acceptable is disclosed in Remington's Pharmaceutical Sciences, 19th ed. Mack Publishing Company, Easton, Pa., 1995.

In addition, the inventive pharmaceutical composition may be formulated by using the method which is known in the art, to provide rapid, continuous or delayed release after administered to a mammalian.

In addition, the stroke imaging composition of the present invention is characterized in that it includes the peptide of the present invention. The stroke imaging composition of the present invention may be used for imaging a stroke by including the peptide of the present invention. In addition, the present invention provides the peptide's uses for imaging a neoplastic disease region. Furthermore, the present invention provides an imaging method for the neoplastic disease region, in which the peptide of the present invention and a label bound thereto are administered to an individual requiring them in an effective dose.

Herein, the imaging and the diagnosis of a disease may be comprehensively used for the progress of a disease, the process of disease treatment, and the monitoring of a response to a therapeutic agent as well as the first medical examination of the disease, but the present invention is not limited thereto. The peptide may be provided with a label in order to easily determine if it is bound, and to easily carry out detection and quantification. This is the same as described above.

In one embodiment of the present invention, it was determined that the peptide of the present invention was specifically bound to the penumbra of a stroke region (see <Example result 3>).

Especially, it is known that as the ratio of a penumbra is higher than an umbra in a stroke region, the possibility of recovery of the region injured by a stroke is increased, thereby showing good prognosis of treatment (Ford G A., Br. J. Pharmacol. 153 (Suppl 1):S112-9, 2008; Segura T. et al., Expert. Opin. Pharmacother. 9:1071-1085, 2008). Accordingly, the stroke imaging composition comprising the peptide of the present invention can be usefully used for imaging, detecting, and quantifying a penumbra, and In addition can be usefully used for predicting the prognosis of drug treatment by measuring the relative size and extent of the penumbra and the umbra through a conventional penumbra imaging technology.

For easy identification, detection and qualification of binding the peptide of the present invention, the peptide of the present invention may be provided as a form of labeled. In other words, the peptide could be provided with linked (for example, covalent bond or crosslink) to a detectable label material. The detectable label material may be preferably selected from the group consisting of, but not limited thereto, ultrasuper paramagnetic particles (for example, iron oxide) which is used in Magnetic Resonance Imaging (MRI) and super paramagnetic particles, radioactive isotope (for example, $^{124}$I, $^{18}$F, $^{11}$C, $^{64}$Cu) which is used in Positron Emission Tomography (PET), radioactive isotope (for example, $^{99m}$Tc, $^{131}$I, $^{125}$I) which is used in gamma camera and other radioactive isotopes (for example, $^{32}$P, $^{35}$S), luminous material or fluorescent material (Cy7.5, Cy5.5, FITC, RITC), coloring enzyme (for example, peroxidase, alkaline phosphatase), chromophore. The label may be performed while peptide synthesis steps of the present invention or may be performed additional to already synthesized peptide.

The amount of the peptide of the present invention comprised in a composition of the present invention varies depending on the kind and the amount of a reagent for treatment of stroke which binds thereto. Preferably, the amount of the peptide may be that of which could deliver the reagent for treatment of stroke thoroughly to stroke tissue. However, since effective administration amount for a patient is determined by considering age, body weight, health condition, sex, severity of the disease, diet and excretion, if the aspects were considered, the person skilled in the art could determine effective amount of the peptide of the present invention for treatment of stroke with binding a reagent for treatment of stroke thereto. A composition of the present invention may comprise an appropriate buffer to maintain/preserve the stability of the peptide.

The composition comprising the peptide of the present invention does not limited its formulation, administration route and administration method as far as it shows effect. For example, the peptide of the present invention may be administered orally or parenterally. In case of oral administration, it is preferable to formulate the peptide of the present invention to D-form amino acid to prevent degradation by gastric enzymes. As the parenteral administration, it may be hypodermic injection, intra-muscular injection, intra-venous injection, intra-arterial injection, and preferably it may be intra-venous injection or intra-arterial injection.

Besides, a pharmaceutical composition of the present invention may be prepared by formulated into general forms with pharmaceutically acceptable carriers. As used herein, the term "pharmaceutically acceptable" means physiologically acceptable and, when administered to human beings or animals, generally does not cause allergic reactions, such as gastrointestinal disorder and dizziness, or similar reactions thereto. The pharmaceutically acceptable carriers for injectable formulation could be a buffer, preservative, painless agent, solubilizer, isotonic agent and stabilizer. Likely, various formulations of the composition comprising the peptide of the present invention may be prepared as the above-mentioned. For example, in case of injectable formulation, it may be prepared as a form of single dose ampoule of multi dose agent. The composition for drug delivery comprising the peptide of the present invention may be administered by the method well known in the art.

The administration amount of the pharmaceutical composition of the present invention may be suitably determined by considering administration route, administration subject, the subject disease and severity thereof, age, sex, body weight, variation of the individuals, and health condition. Preferably, the pharmaceutical composition of peptide of the present invention may vary depending on the severity of the disease, but the effective ingredient may be generally administered at an effective dose of 10 µg-10 mg several times daily.

Advantageous Effects

As can be seen from the foregoing, the peptide of the present invention can be useful in diagnosis of stroke. Diagnosis of stroke using the peptide of the present invention may diagnose stroke more easily and more precisely when it compared with prior diagnosis methods. In addition, if diagnosis of stroke of the present invention is performed with prior diagnosis methods, it is effective in early diagnosis and early detection of the relapse. In addition, the peptide of the present invention can be useful as a drug delivery carrier. That is, when the peptide of the present invention is bound to an agent for treating stroke, the agent is delivered to the stroke tissue selectively and then the peptide has effect of increasing effectiveness of the agent and decreasing side effect.

BRIEF DESCRIPTION OF DRAWINGS

A: the photograph showing the tact that After middle cerebral artery obliterans, ipsilateral hemisphere exhibit white color which indicate ischemic cell damage, while contralateral hemisphere exhibit strong red color which indicate live cell by TTC staining.

B: the photograph showing CLEVSRKNC peptide (SEQ ID NO: 1) is targeted to ipsilateral hemisphere.

C: the photograph showing CLEVSRKNC peptide (SEQ ID NO: 1) is not targeted to contralateral hemisphere.

D: the photograph showing scrambled peptide is not observed in ipsilateral hemisphere.

E: the photograph showing scrambled peptide is not observed in contralateral hemisphere.

F,G,H: the photograph showing CLEVSRKNC (SEQ ID NO: 1) peptide does not home to control group organs such as spleen, liver and lung.

I: the photograph showing cell existing region by DAPI staining.

J: the photograph showing apoptotic cell existing region by TUNEL staining.

K: the photograph showing fluorescent region by binding with CLEVSRKNC peptide (SEQ ID NO: 1).

L: the photograph showing that most of TUNEL-positive apoptotic cells except some cells bind to CLEVSRKNC peptide (SEQ ID NO: 1) by merging photograph J and K.

A to C: the photograph showing CLEVSRKNC peptide (SEQ ID NO: 1) is located in the same position with β-tubulin-positive neuron cell in ischemic brain tissue.

D to F: the photograph showing CLEVSRKNC peptide (SEQ ID NO: 1) is not observed in contralateral hemisphere which is not ischemic brain tissue.

G to I: the photograph showing CLEVSRKNC peptide (SEQ ID NO: 1) is not located in the same position with GFAP-positive astrocyte in ischemic brain tissue.

J to L: the photograph showing CLEVSRKNC peptide (SEQ ID NO: 1) is not observed in contralateral hemisphere which is not ischemic brain tissue.

A: the photograph showing absorption of $^{131}$I-CLEVSRKNC peptide (SEQ ID NO: 1) is observed only in ipsilateral hemisphere.

B: the photograph showing the absorption of $^{131}$I-scrambled control peptide is observed with much lower concentration compared with $^{131}$I-CLEVSRKNC peptide (SEQ ID NO: 1) in ipsilateral hemisphere.

C: the photograph showing the absorption of $^{131}$I-CLEVSRKNC peptide (SEQ ID NO: 1) in normal brain of the rat of negative control group is comparatively low.

D: the photograph showing the absorption of $^{131}$I-CLEVSRKNC peptide (SEQ ID NO: 1) in ischemic tissue reaches to highest peak at $3^{rd}$ day after ischemic damage.

E: the graph showing absorption rate of $^{131}$I-CLEVSRKNC peptide (SEQ ID NO: 1) reaches to highest peak at $3^{rd}$ day after ischemic damage by measuring light-stimulating luminous degree.

EMBODIMENTS OF THE INVENTION

Hereafter, the present invention will be described in detail.

However, it is to be understood that the following examples are illustrative only and the present invention is not limited thereto.

1. A Gnawing Animal Model of Focal Cerebral Ischemia

All animal tests were carried out under the guideline of experimental ethics committee of the subject organization of the present inventor. A grown male sprague-dawle rat (Hyochang Science, Daejeon, Korea) with a weight of 290 to 320 g was anesthetized by inhalation of enflurane in 80% $N_2O$/ 20% $O_2$ during a surgical operation. First, a left-side carotid artery and a bifurcation thereof were separated. An uncoated 30 mm section of round-ended 3-0 nylon suture was inserted into the root of the carotid artery and then was advanced into an internal carotid artery of about 20 mm from an internal carotid artery bifurcation. Then, the state where the inlet of a middle cerebral artery (MCA) was blocked was left for 2 hours. At about the time when the ischemic duration was ended, the suture was removed. Then, the animal of which MCA was temporarily occluded was subjected to perfusion again and then was subjected to a detailed analysis

2. In Vivo Screening of Phage Library

A phage peptide library based on a T7 415-1b phage vector displaying CX7C (C: cysteine; X: random peptide) was obtained under the guideline of a manufacturer (Novagen, Madison, Wis., USA). The library has a variety of about $5 \times 10^8$ plaque forming units (PFU).

After 2 hours from reperfusion following the occlusion of the MCA, the phage library ($5 \times 10^{11}$ pfu/500 µl culture medium) was injected through a tail vein of the rat and was circulated for 2 hours. After the circulation, 50 ml of phosphate-buffered saline (PBS) was perfused through the heart of the rat in the anesthesia state. The brain was separated, and an ipsilateral (injured) hemisphere and a contralateral (uninjured) hemisphere were separated, and then they were placed on a medium of Dulbecco's modified Eagle's medium (DMEM)/1% bovine serum albumin (BSA). The tissue placed in the medium of DMEM/1% BSA was homogenized by using a medimachine device (DAKO, USA), and then washed three times in a medium of ice-cold DMEM/1% BSA. The phage attached on the tissue was recovered through infection of E. coli and then amplified for screening in the next round. After the screening in the 3rd round, phage clones were randomly selected, and their insertion DNA sequences were determined (Koma Biotech Co., Daejeon, Korea). Then, peptide sequences corresponding to the DNA sequences were translated. In order to determine motifs shared by amino acid sequences, a program of Clustal W was used to the analysis. In addition, in order to determine proteins having the homologous motifs were analyzed by an NCBI BLAST search program.

In order to test each of phage clones, each phage clone ($5 \times 10^{11}$ pfu/500 µl culture medium) was injected into a tail vein of the rat which has been left for 24 hours from ischemic injury. After 2-hour circulation, the rat was subjected to perfusion by PBS through the heart, and then its brain was separated. Next, an ipsilateral hemisphere and a contralateral hemisphere were separated, and a titer of the phage attached on the tissue was measured by plaque assay.

3. In Vivo Targeting of Peptide and Immunofluorescence Method

The present inventors synthesized a peptide with N-terminal labeled by fluorescein in accordance with a standard Fmoc method through the entrustment to a specialty company (Anygen Co., Kwangju, Korea). A predetermined amount of peptide was injected in a concentration of 1 mmol/L in 500 µl of PBS to a left ventricle of the rat which has been left for 24 hours from ischemic injury. After 15-minute circulation, the rat was perfused with PBS, and then perfused again with 4% of paraformaldehyde (PFA). The brain was separated from other organs, prepared for a frozen section, and then was sequentially cut with a thickness of 10 µm. For counter staining of a nucleus, it was transferred to a medium containing DAPI (4,6-diamidino-2-phenylindole) (Vector Laboratories, Berlingame, Calif.), and the tissue slide was observed by a fluorescence microscope (Zeiss, Oberkochen, Germany).

In order to determine the type of cells bound to the peptide, the sections were immunostained by anti-tubulin (Chemicon, Temecula, Calif., USA) and anti-GFAP (glial fibrillary acidic protein) cocktail (BD Pharmingen, San Diego, Calif., USA) antibody at room temperature for 1 hour. Then, a second antibody (Molecular Probe, Carlsbad, Calif.) bound to Alexa594 was reacted at room temperature for 30 minutes.

In order to carry out an analysis on ischemic injury, adjacent sections were stained with TTC (2,3,5-triphenyltetrazolium chloride). TTC is reduced to red formazan by succinate dehydrogenase (as a mitochondrial enzyme) in survived cells, while in injured cells, TTC is white due to destruction of mitochondrial function. Based on the result of TTC staining, a region, which was changed to white through TTC staining on the first day from the injury and then was changed to red after 1 week, was appointed as a penumbra.

4. Radioisotope Labeling of Peptide and Autoradiogram

In order to link a radioisotope $^{131}$I, each peptide was added with a tyrosine (Y) residue at N-terminal during synthesis. The peptide was labeled with [$^{131}$I]NaI by using iodine beads (Pierce Biochemical Co., Rockford, Ill.). [$^{131}$I]NaI (half life=8.0 days) was purchased from Atomic Energy Research Institute (Daejeon, Korea). In brief, the beads were reacted with a [$^{131}$I]NaI (100 MBq) solution in PBS, and then reacted with a peptide solution (14 mg/20 ml, of water) at room temperature for 15 minutes. The introduction ratio of [$^{131}$I], measured by radio-TLC, was 47%. The peptide labeled with [$^{131}$I] was purified at a rate of 1 ml/min by HPLC through a column (Shiseido Capcell Pak C-18) and an elution solvent (solvent A: 0.1% TFA (trifluoroacetic acid) in water, solvent B: 0.1% TFA in acetonitrile, the ratio of solvent A:solvent B was from 97:3 to 20:80 after 30 minutes). The radiochemical purify of a final solution was over 81.2%.

For radiography, the peptide labeled with $^{131}$I was injected through a tail vein of the rat at a predetermined time after the occlusion of MCA. After 1-hour circulation, the rat was subjected to perfusion by PBS through the heart. The brain was separated, and frozen sections were prepared. A tissue slide of 40 µm coronal section was placed on a cassette, and was exposed for 3 days with covering of a general X-ray film or a phosphor imaging plate (Fujifilm Co., Tokyo, Japan). For quantification of radioactivity strength with the passage of time, the phosphor imaging plate was scanned by using a FLA-3000™ phosphor imaging plate scanner (Fujifilm Co.). The region of interest was shown on the image, and the optically stimulated luminescence of the region was calculated by using MultiGauge™ software (Fujifilm Co.).

Example Result

1. Screening of Phage-Displayed Peptide Library

The present inventors carried out in vivo phage display in order to select a phage selectively induced to a stroke lesion in the rat with the occluded MCA. A phage library displaying CX7C random peptide on a virus surface was injected into a tail vein of the rat after 4 hours from ischemic injury (or after 2 hours from 2-hour perfusion of MCA occlusion), and then circulated for 2 hours. An ipsilateral (ischemic) hemisphere of a brain was extracted, and the phage attached on the tissue was recovered and amplified for screening for the next round. After the screening in the 3rd round, the titer of the recovered phage was amplified about 60 times (data not noted). In the second and third rounds, a total of 30 phage clones were randomly selected. The base sequences of insertion DNA coding the peptide were scanned and translated into peptide sequences through the entrustment to a specialty company (Bionia, Daejeon). As a result of the analysis on arrangement of peptide sequences using a Clustal W program, frequently occurring sequences, such as CLEVSRKNC (SEQ ID NO: 1), CKRGGATAC (SEQ ID NO: 2), and CRSAVAKNC (SEQ ID NO: 3), were found (see Table 1). In addition, in Table 1, examples of rat proteins comprising homologous motifs of peptides searched for from Swissprot database are noted. The phage-displayed peptide may be bound to a stroke tissue through mimicry of one or more of these proteins.

TABLE 1 examples of rat proteins including homologous motifs to peptide sequences

| Peptide sequence | Frequency (%) | Example of rat protein (homologous motif) | Accession No. |
|---|---|---|---|
| CLEVSRKNC (SEQ ID NO: 1) | 9/30 (30%) | Neuronal voltage-gated calcium channel gamma-3 subunit ($^{49}$ETSRKN$^{54}$) (SEQ ID NO: 5) | Q8VHX0 |
| | | Potassium channel subfamily T member 2 ($^{1121}$EPSRKN$^{1126}$) (SEQ ID NO: 6) | Q6UVM4 |
| | | Stress 70 protein chaperone microsome-associated 60 kDa protein ($^{364}$EVSRK$^{368}$) (SEQ ID NO: 7) | O35162 |
| CKRGGATAC (SEQ ID NO: 2) | 7/30 (23%) | Neuronal voltage-gated calcium channel gamma-6 subunit ($^{254}$KRGGPTA$^{260}$) (SEQ ID NO: 8) | Q8VHW7 |
| CRSAVAKNC (SEQ ID NO: 3) | 5/30 (17%) | Thyroid receptor-interacting protein 15 ($^{100}$RSAVTRN$^{106}$) (SEQ ID NO: 9) | P61203 |
| CTKRNAPDC (SEQ ID NO: 4) | 3/30 (10%) | Nerve growth factor-inducible protein PC4 ($^{6}$KRNAP$^{10}$) (SEQ ID NO: 10) | P20695 |

2. Targeting of CLEVSRKNC-Phage (CLEVSRKNC is Identified as SEQ ID NO: 1) to an Ischemic Stroke Tissue in a Living Body The present inventors found that a phage displaying a CLEVSRKNC peptide (SEQ ID NO: 1) was targeted to the stroke tissue in the living body. The CLEVSRKNC sequence (SEQ ID NO: 1) was preferentially applied in the following research, because it is most frequently occurring sequence in the selected peptide sequence (Table 1). The CLEVSRKNC-phage (CLEVSRKNC is identified as SEQ ID NO: 1) was intravenously injected into a rat after 24 hours from ischemic injury (or after 22 hours from 2-hour perfusion of MCA occlusion), or into a general control group rat. After 2-hour circulation, an ipsilateral (ischemic) hemisphere and a contralateral (non-ischemic) hemisphere were separated, and each attached phage was recovered.

Figure 1:
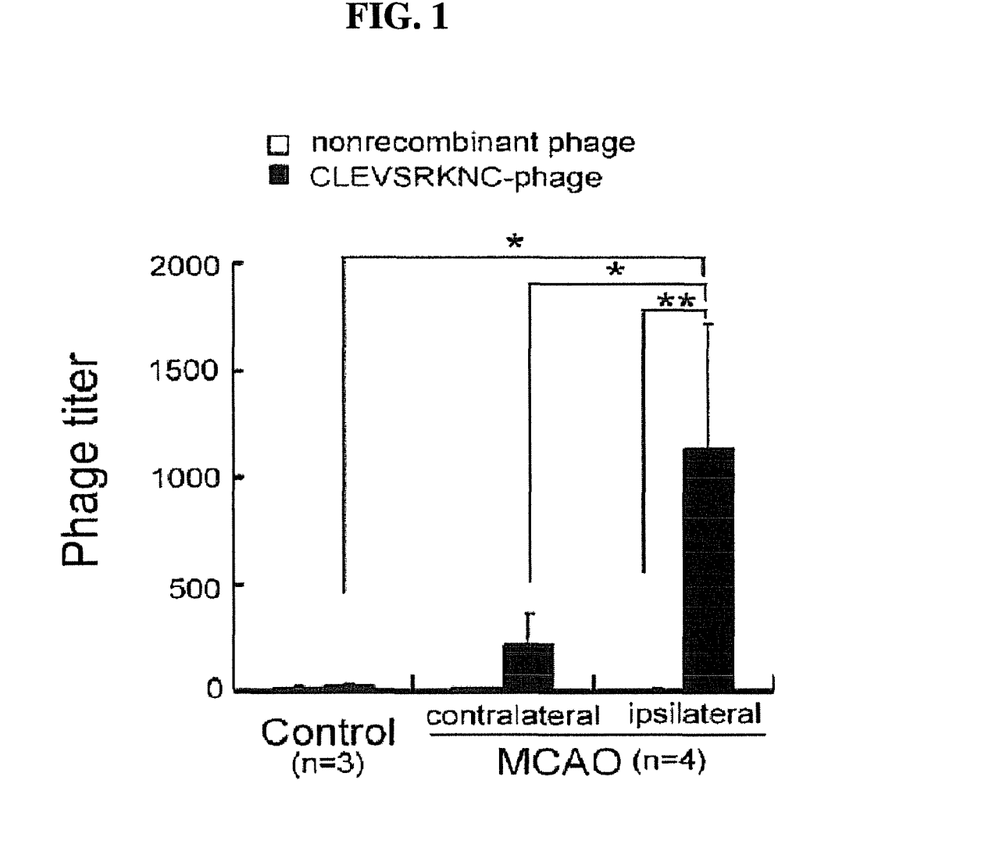
FIG. 1 is the graph showing that CLEVSRKNC-phage is targeted to the ipsilateral hemisphere which is stroke tissue in vivo (MCAO: middle cerebral artery obliterans, *:P<0.05, **:P<0.01). CLEVSRKNC is the amino acid sequence identified as SEQ ID NO: 1.

As a result, the titer of CLEVSRKNC-phage (CLEVSRKNC is identified as SEQ ID NO: 1) targeted to the ipsilateral brain tissue was about 5.3 times higher than the contralateral tissue in the rat with occluded MCA, and was 68 times higher than a normal brain tissue of the control group rat ($P<0.05$, see FIG. 1). The titer of the non-recombinant control group phage targeted to the ipsilateral or contralateral tissue was significantly smaller than CLEVSRKNC-phage ($P<0.01$, see FIG. 1) (CLEVSRKNC is identified as SEQ ID NO: 1).

3. Targeting of CLEVSRKNC Peptide (SEQ ID NO: 1) to an Ischemic Stroke Tissue in a Living Body, and Detection of Apoptosis The present inventors determined if the selective targeting of CLEVSRKNC-phage (CLEVSRKNC is identified as SEQ ID NO: 1) to a stroke tissue was done through the peptide displayed on a phage. A CLEVSRKNC peptide (SEQ ID NO: 1) bound to fluorescein, and a CNSREVLKC peptide including scrambled amino acid sequences as a control group peptide were synthesized. They were administered into a left ventricle of a rat which has been left for 24 hours from ischemic injury, and were circulated for 15 minutes.

As a result, after TTC staining following MCA occlusion, the left-side ipsilateral hemisphere was not stained and showed a white color indicating ischemic cell injury, while the right-side contralateral hemisphere showed a deep red color indicating a survived cell (see FIG. 2A).

Through fluorescence microscopic observation on frozen sections, it was proved that the CLEVSRKNC peptide (SEQ ID NO: 1) was not targeted to the contralateral tissue (see FIG. 2C), and was targeted to the ipsilateral tissue (see FIG. 2B). Interestingly, the targeting of the peptide was observed in a penumbra between the ischemic center portion and its peripheral non-ischemic tissue, as indicated by the box in FIG. 2A. On the other hand, the targeting of the amino acid sequence of a control group was not observed in the ipsilateral or contralateral tissue (see FIGS. 2D and 2E). The targeting of CLEVSRKNC peptide (SEQ ID NO: 1) to control group organs, such as a spleen, a liver, and a lung, was little (see FIGS. 2F to 2H). In the analysis on targeting within a living body, similar results were obtained from 5 rats. In the similar manner as that of the 15-minute circulation test, the CLELVSRKNC peptide was targeted to the ischemic hemisphere through 2-hour circulation (data not noted).

Through the analysis of apoptosis using TUNEL staining on DNA fragments, it was observed that many cells of a penumbra were apoptotic cells stained by TUNEL while survived cells not stained by TUNEL still exist (see FIGS. 2I and 2J). In the region, most of the apoptotic cells stained with TUNEL, except for some of them, were bound to CLELVSRKNC peptide (see FIGS. 2J to 2L). Through this result, it was found that the CLELVSRKNC peptide can detect the apoptosis in the penumbra of an ischemic brain tissue, and thus can be usefully used for imaging, detecting, and quantifying the penumbra. In addition, it was found that the peptide can measure relative sizes and extents of the penumbra and the umbra by using a conventional imaging technology of the penumbra, and thus can be usefully used for predicting the prognosis of drug treatment.

4. Distribution of CLEVSRKNC Peptide (SEQ ID NO: 1) in an Ischemic Stroke Tissue The present inventors analyzed the distribution of the CLEVSRKNC peptide (SEQ ID NO: 1) in the ischemic stroke tissue, in vivo induced, that is, the type of cells bound to the peptide. The immunofluorescence staining method using an antibody specific to a cell type showed that the fluorescent CLEVSRKNC peptide (SEQ ID NO: 1) corresponded to the position of β-tubulin-positive neuron cell in the ischemic brain tissue (see FIGS. 3A to 3C), but did not correspond to GFAP-positive astrocyte (see FIGS. 3G to 3I). As expected, the targeting of CLEVSRKNC peptide (SEQ ID NO: 1) was not observed in a neuron cell and an astrocyte in the contralateral brain tissue (see FIGS. 3D and 3J). The cell bound to the peptide after 24 hours from ischemic injury had a similar shape as a neuron, while destruction or contraction of a neuron cell shape, shown through β-tubulin staining, was higher in the ipsilateral tissue, compared to that in the contralateral tissue (see FIGS. 3B and 3E). In addition, the expression of GFAP with an increased level in an astrocyte was observed in the ischemic tissue (see FIGS. 3H and 3K).

5. Autoradiogram on Absorption of CLEVSRKNC Peptide (SEQ ID NO: 1) in an Ischemic Stroke Tissue The present inventors imaged the absorption of CLEVSRKNC peptide (SEQ ID NO: 1) labeled with a radioisotope in a rat's ischemic tissue with occluded MCA. A $^{131}$I-labeled CLEVSRKNC peptide (SEQ ID NO: 1) or a scrambled control group peptide was injected to a tail vein of the rat which has been left for 24 hours from ischemic injury, and then was circulated for 1 hour. The entire brain was separated and was subjected to autoradiogram analysis.

As a result, the selective absorption of $^{131}$I-CLEVSRKNC peptide (SEQ ID NO: 1) was observed in the ipsilateral hemisphere, while the absorption was insufficient in the contralateral region (see FIG. 4A) and a general brain of a control group rat (see FIG. 4C). It was observed that the absorption of $^{131}$I-control group peptide showed a very low concentration in the ipsilateral hemisphere, compared to CLEVSRKNC peptide (see FIG. 4B) (SEQ ID NO: 1).

In the absorption of $^{131}$I-CLEVSRKNC peptide (SEQ ID NO: 1) with the passage of time, the absorption was increased on the first day from the ischemic injury in an ischemic tissue, reached a peak on the third day, and reduced on the seventh day (see FIG. 4D). This was supported by the measurement of optically stimulated luminescence in which 4 coronal sections showed a very high absorption rate on the third day from the injury compared to those on the first day and the seventh day (P<0.01, see FIG. 4E). The average absorption ratio of the ischemic tissue to the control group tissue was about 2:1 in each time period after ischemic injury (P<0.05 or P<0.01, see FIG. 4E).

INDUSTRIAL APPLICABILITY

As can be seen from the foregoing, the peptide of the present invention can be useful in diagnosis of stroke. Diagnosis of stroke using the peptide of the present invention may diagnose stroke more easily and more precisely when it compared with prior diagnosis methods. In addition, if diagnosis of stroke of the present invention is performed paralleling with prior diagnosis methods, it is effective in early diagnosis and early detection of the relapse. In addition, the peptide of the present invention can be useful as a drug delivery carrier. That is, when the peptide of the present invention is used with linking a reagent for treatment of stroke, the reagent is delivered to the stroke tissue selectively and has effect of increasing effectiveness of the drug and decreasing side effect.

The invention claimed is:

1. An isolated stroke-targeting peptide comprising the amino acid sequence selected from the group consisting of SEQ ID NO: 1, SEQ ID NO: 2, SEQ ID NO: 3, and SEQ ID NO: 4.

2. A vector comprising a nucleotide sequence encoding the isolated stroke-targeting peptide of claim 1.

3. A method for drug delivery comprising administering to a subject in need thereof an effective amount of the peptide of claim 1 and an agent bound thereto.

4. A method for treating stroke comprising administering to a subject in need thereof an effective amount of the peptide of claim 1 and an anti-stroke agent bound thereto.

5. The method of claim 4, wherein the anti-stroke agent is selected from the group consisting of a calcium channel blocker, glutamate, an NMDA receptor antagonist, an antioxidant, an apoptosis inhibitor, and minocycline-based antibiotics.

6. A method for diagnosis of stroke comprising the steps of:
   (a) administering to a subject in need thereof an effective amount of the peptide of claim 1 and a label bound thereto, wherein the label is selected from the group consisting of chromogenic enzymes, radioisotopes, chromophores, light emitting materials, fluorescers, super paramagnetic particles, and ultrasuper paramagnetic particles; and
   (b) determining binding of the peptide to a stroke cell thereby determining the site of binding in the subject.

7. The method of claim 6, wherein stroke is ischemic stroke.

8. The method of claim 6, wherein stroke is penumbra region of stroke.

9. A method for imaging stroke lesion comprising administering to a subject in need thereof an effective amount of the peptide of claim 1 and a label bound thereto, wherein the label is selected from the group consisting of chromogenic enzymes, radioisotopes, chromophores, light emitting materials, fluorescers, super paramagnetic particles, and ultrasuper paramagnetic particles.

10. The method of claim 9, wherein stroke is ischemic stroke.

11. The method of claim 9, wherein stroke is penumbra region of stroke.

\* \* \* \* \*